US00PP23822P3

(12) United States Plant Patent
Olesen

(10) Patent No.: US PP23,822 P3
(45) Date of Patent: Aug. 13, 2013

(54) MINIATURE ROSE PLANT NAMED 'POULPAR065'

(50) Latin Name: ***Rosa* hybrid**
Varietal Denomination: Poulpar065

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 8 days.

(21) Appl. No.: 13/317,256

(22) Filed: Oct. 13, 2011

(65) Prior Publication Data

US 2013/0097747 P1 Apr. 18, 2013

(51) Int. Cl.
*A01H 5/00* (2006.01)

(52) U.S. Cl.
USPC ..... Plt./118; Plt./116

(58) Field of Classification Search
USPC ..... Plt./116, 118
See application file for complete search history.

(56) References Cited

PUBLICATIONS

UPOV-PLUTO plant variety database, 2012-05, retrieval software, citation for 'POULPAR065' (2 pages).*
Community Plant Variety Office, Application for Plant Breeder'S Rights 20100223, 7 Pages.

* cited by examiner

*Primary Examiner* — Susan McCormick Ewoldt

(57) ABSTRACT

A new miniature rose plant that has abundant, yellow flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar065'.

SUMMARY OF THE INVENTION

The present invention constitutes a new and distinct variety of miniature rose plant which originated from a controlled crossing between the female seed parent, an unnamed seedling, and the male pollen parent, an unnamed seedling.

The two parents were crossed during the summer of 2006 and the resulting seeds were planted in a controlled environment in Fredensborg, Denmark. The new variety, named 'Poulpar065', originated as a single seedling from the stated cross.

The new variety may be distinguished from its female seed parent primarily by plant height. The female seed parent is 10 cm taller than the new variety.

The new variety may be distinguished from its male pollen parent primarily by flower color. The male parent has light yellow flowers while the new variety has medium yellow flowers.

The objective of the hybridization of this rose variety for commercial culture was to create a new and distinct variety with unique qualities, such as:

1. Uniform and abundant yellow flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar065' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar065' was selected by the inventor as a single plant from the progeny of the hybridization in 2006.

Asexual reproduction of 'Poulpar065' by cuttings and traditional budding was first done by Mogens N. Olesen in the nursery in Fredensborg, Denmark in June of 2007. This initial and other subsequent propagations conducted in controlled environments have demonstrated that the characteristics of 'Poulpar065' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar065'.

DETAILED DESCRIPTION OF THE VARIETY

The following is a description of 'Poulpar065', as observed in its growth in glasshouses in Half Moon Bay, Calif. Observed plants are 10 weeks of age and were cultivated in 10.5 cm pots. Color references are made using The Royal Horticultural Society (London, England) Colour Chart, 2001, except where common terms of color are used.

For a comparison, several physical characteristics of the rose variety 'Poulmist', U.S. Plant Pat. No. 18,975. are compared to 'Poulpar065' in Chart 1.

CHART 1

| | 'Poulpar065' | 'Poulmist' |
|---|---|---|
| Petal count: | 80 to 90 | 35 to 40 |
| Flower Diameter: | 50 to 55 mm | 40 mm |
| General Tonality of Flower Color: | Yellow Group 10B with intonations of Yellow Group 13C | Yellow Group 12B |

FLOWER AND FLOWER BUD

Blooming habit: Continuous.

Flower bud:

*Size*.—Upon opening, 22 mm in length from base of receptacle to end of bud. 13 mm in diameter.

*Bud form*.—Ovate.

*Bud color*.—As sepals unfold, petals are Yellow Group 8C.

*Sepals*.—Upper Surface: Color: Yellow-Green Group 147A. Texture: Smooth and somewhat pubescent. Lower Surface: Color: Yellow Green Group 144A and Yellow-Green Group 147A. Texture: Smooth. Shape: Apex: Cirrhose. Base: Flat at union with receptacle. Margins: Margins have moderate foliaceous appendages on three of the five sepals. Size: 35 mm long by 6 mm wide.

*Receptacle*.—Surface Texture: Smooth. Shape: Campanulate. Size: 5 mm in height by 6 mm wide. Color: Yellow-Green Group 144A.

*Pedicel*.—Surface: Smooth. Length: 20 mm average length. Diameter: 3 mm. Color: Yellow-Green Group 144A. Strength: Medium strength.

*Borne*.—Singly.

Flower bloom:

*Fragrance*.—Moderate floral scent.

*Duration*.—As a pot plant, flowers last about 25 days. Petals do not fall cleanly away from plant.

*Size*.—Flower diameter is 50 to 55 mm and 15 mm deep.

*Form*.—General shape is rosette with many slightly overlapping petals of different sizes.

Petalage: There are normally 80 to 90 petals, 15 of which are petaloids.

Petal color:

*Upon opening*.—Innermost and outermost petals are Yellow Group 10A on the upper surface and Yellow Group 10B on the lower surface. Occasionally, the guard petals are Yellow-Green Group 145C and Green Group 141C at the upper and lower surfaces. No distinctive coloration at petal base observed.

*After opening*.—Innermost and outermost petals are Yellow Group 10A on the upper surface and Yellow Group 10C on the lower surface. Occasionally, the guard petals are Yellow-Green Group 145C and Green Group 141C at the upper and lower surfaces. No distinctive coloration at petal base observed.

General tonality: Yellow Group 10B with intonations of Yellow Group 13C.

Petals:

*Petal reflex*.—Moderate.

*Petal margin*.—Entire with a point at the center. Moderate undulations observed.

*Shape*.—Generally broadly elliptic. Base: Acute. Apex: Rounded and cuspidate.

*Size*.—Outer petals are 26 mm long by 26 mm wide. Inner petals are 15 mm long by 10 mm wide.

*Thickness*.—Average.

Petaloids:

*Quantity*.—15 on average.

*Size*.—15 mm long; 8 mm wide.

*Shape*.—Apex is rounded. Base is acute. Generally the petaloids are symmetric.

*Color*.—Yellow Group 10A on the upper surface and Yellow Group 10C on the lower surface.

Reproductive organs:

*Pollen*.—None observed.

*Anthers*.—Size: 2 mm long. Color: Yellow Group 11A. Quantity: 30 on average.

*Filaments*.—Color: Yellow Group 7C. Length: 4 mm.

*Pistils*.—Length: 5 mm long. Quantity: 25 on average.

*Stigmas*.—Level relative to the length of the filaments and the height of the anthers. Color: Greyed-Yellow Group 161C.

*Styles*.—Color: Green-White Group 157C.

*Seed formation*.—Not observed.

PLANT

Plant growth: Upright. When grown as a 10.5 cm pot plant on its own roots, the average height of the plant itself is 18 cm and the average width is 15 cm.

Stems:

*Color*.—Young wood: Yellow-Green Group 144A. Older wood: Yellow-Green Group 144A.

*Internodal distance*.—30 mm on average.

*Length of stems*.—From the base of the plant to the flowering portion is about 13 cm.

*Stem diameter*.—3 mm.

*Surface texture*.—Young wood: Smooth. Older wood: Smooth.

Prickles: None. Observed plants are without prickles.

Plant foliage: Number of leaflets on normal leaves in middle of the stem is 5 or 7 leaflets.

*Compound leaf size*.—75 mm (l)×50 mm (w)

*Quantity*.—2 to 3 leaves per 10 cm of stem.

*Color*.—Juvenile foliage: Upper Leaf Surface: Yellow-Green Group 146A. Lower Leaf Surface: Yellow-Green Group 147B. Mature foliage: Upper Leaf Surface: Yellow-Green Group 147A. Lower Leaf Surface: Yellow-Green Group 147D.

Plant leaves and leaflets:

*Stipules*.—Size: 6 mm in length. Shape: Linear, slightly broad based with outward extending apices. Margins: Entire. Color: Yellow-Green Group 147A.

*Petiole*.—Length: 15 mm long by 1 mm wide. Color: Upper surface is Yellow-Green Group 146A. Lower surface is Yellow-Green Group 144A. Underneath: Smooth.

*Rachis*.—Size: About 25 mm long. Color: Upper surface is Yellow-Green Group 146A. Lower surface is Yellow-Green Group 144A. Underneath: Smooth.

*Leaflet*.—Size: Terminal leaflets are 35 mm length by 18 mm wide on average. Margin: Serrate. General Shape: Elliptical. Apex Shape: Acute. Base Shape: Round. Texture: Smooth. Arrangement: Odd pinnate. Venation: Reticulate. Leaf Gloss: Matte finish.

Disease resistance: Average resistance to powdery and downy mildew, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpar065', substantially as illustrated and described herein, due to its abundant, yellow flowers, vigorous growth, compact habit, suitability for production from softwood cuttings in pots, and durable flowers and foliage that make the variety suitable for distribution in the floral industry.

* * * * *

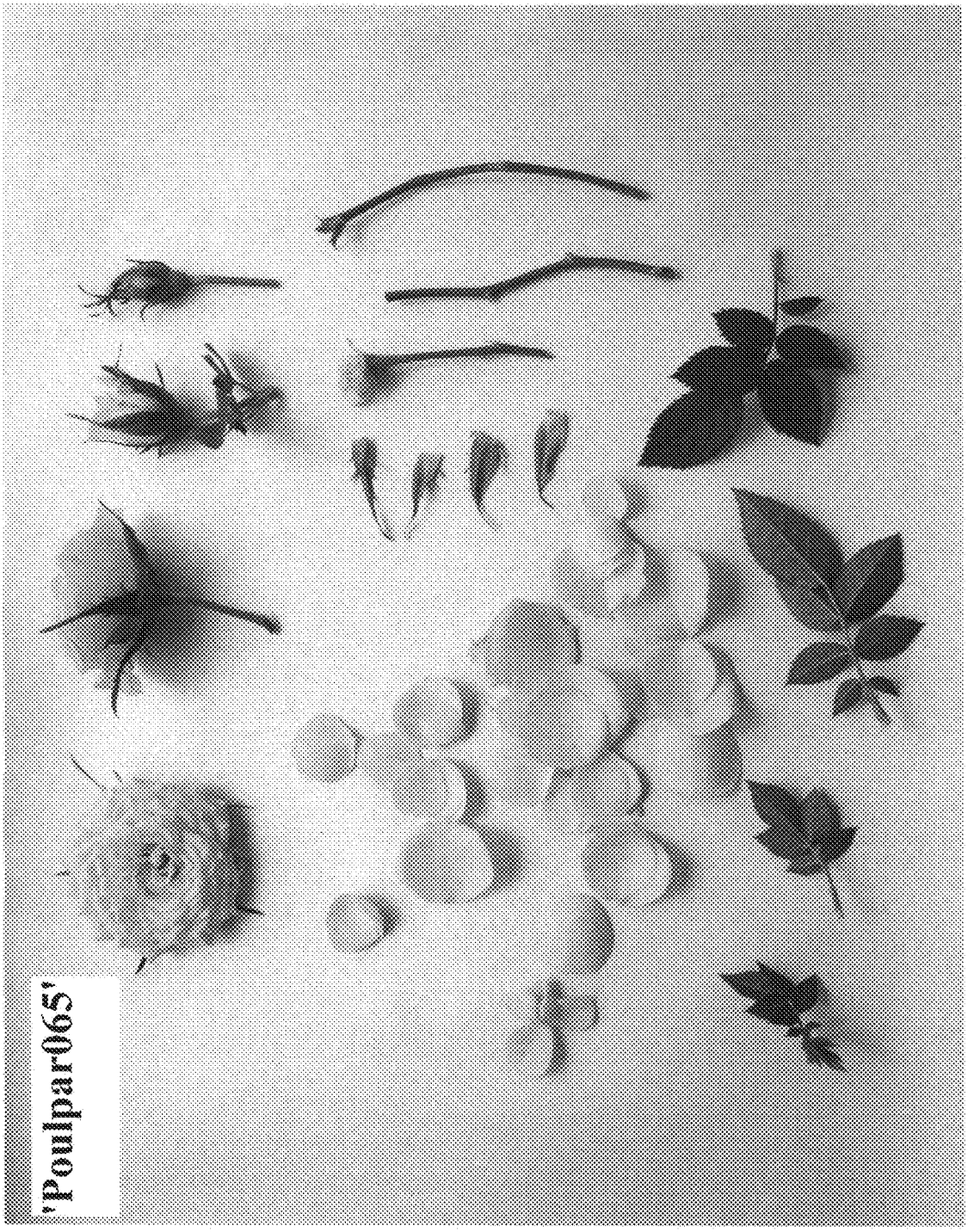
'Poulpar065'